(12) United States Patent
Itoman

(10) Patent No.: US 6,398,787 B1
(45) Date of Patent: Jun. 4, 2002

(54) CABLE SLEEVE SYSTEM FOR BONE FIXATION

(75) Inventor: Moritoshi Itoman, Kanagawa (JP)

(73) Assignee: AI Medic Co., Ltd., Tokyo (JP)

( * ) Notice: Subject to any disclaimer, the term of this patent is extended or adjusted under 35 U.S.C. 154(b) by 0 days.

(21) Appl. No.: 09/622,437

(22) PCT Filed: Feb. 18, 1999

(86) PCT No.: PCT/JP99/00704

§ 371 Date: Nov. 22, 2000

(87) PCT Pub. No.: WO99/42050

PCT Pub. Date: Aug. 26, 1999

(30) Foreign Application Priority Data

Feb. 18, 1998 (JP) ............................... 10-051315

(51) Int. Cl.⁷ ................................ A61B 17/56
(52) U.S. Cl. ........................................ 606/103
(58) Field of Search ................. 606/60, 53–59, 606/61, 72, 75, 103, 67, 69, 70, 71

(56) References Cited

U.S. PATENT DOCUMENTS

| | | | |
|---|---|---|---|
| 3,997,138 A | * 12/1976 | Crock et al. | 248/67.5 |
| 4,269,180 A | * 5/1981 | Dall et al. | 128/92 B |
| 4,567,884 A | * 2/1986 | Edwards | 128/69 |
| 4,950,269 A | 8/1990 | Gaines, Jr. | |
| 5,190,543 A | 3/1993 | Schläpfer | |
| 5,269,784 A | * 12/1993 | Mast | 606/69 |
| 5,499,983 A | 3/1996 | Hughes | |
| 5,643,260 A | * 7/1997 | Doherty | 606/61 |
| 5,713,903 A | * 2/1998 | Sander et al. | 606/72 |
| 5,779,707 A | * 7/1998 | Bertholet et al. | 606/75 |
| 5,863,293 A | 1/1999 | Richelsoph | |
| 6,120,505 A | * 9/2000 | Huedner | 606/74 |

FOREIGN PATENT DOCUMENTS

| | | |
|---|---|---|
| EP | 0323429 A1 | 7/1989 |
| EP | 0582857 A1 | 2/1994 |
| EP | 0811357 A1 | 12/1997 |
| EP | 0878171 A1 | 11/1998 |
| JP | 52-116083 | 9/1977 |
| JP | 6-41710 | 6/1994 |
| JP | 7-184921 | 7/1995 |
| JP | 8-322849 | 12/1996 |
| JP | 10-52440 | 2/1998 |

OTHER PUBLICATIONS

Patent Abstracts of Japan, 7–184921, http://www2.ipdl.jpo–miti.go.jp/dbpweb/connector/guest/DB-Pquery/ENGDB/wdispaj, Aug. 9, 2000.
Patent Abstracts of Japan, 10–52440, http://www2.ipdl.jpo–miti.go.jp/dbpweb/connecter/guest/DB-Pquery/ENGDB/wdispaj, Aug. 9, 2000.

* cited by examiner

*Primary Examiner*—Eduardo C. Robert
(74) *Attorney, Agent, or Firm*—Skjerven Morrill LLP; David W. Heid

(57) ABSTRACT

A cable sleeve system for bone fixation, comprising a cable, and a sleeve including a head for securing the cable and a piercing portion, wherein the piercing portion projects from a bottom face of the head substantially perpendicularly therefrom, and the head is provided with a bore extending in parallel with the bottom face for securing the cable therein, the head being adapted to be crimped to secure the cable therein. Because the sleeve can be made highly compact, it is possible to avoid undesirable side effects such as hemorrhage and inflammation due to irritations to the human body tissues which occurred frequently in the case of the cable securing method using the conventional cable grip.

16 Claims, 3 Drawing Sheets

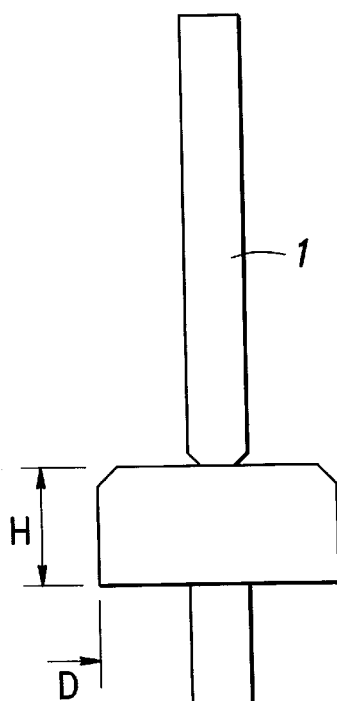
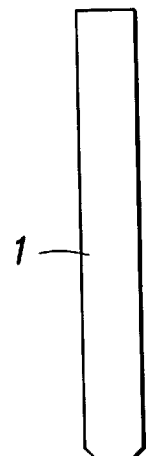
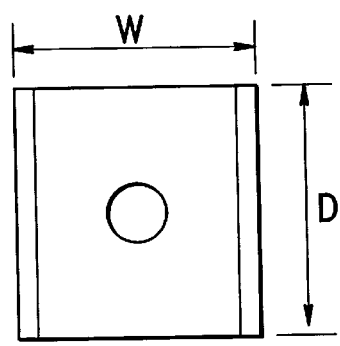
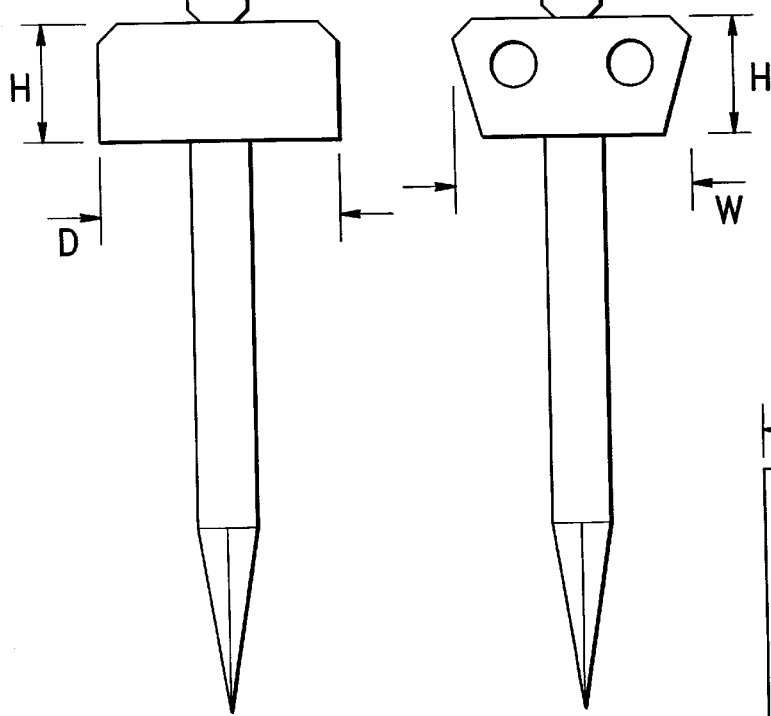
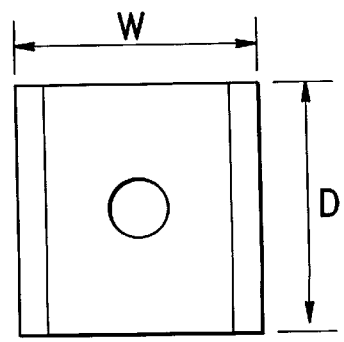
Fig. 1A Fig. 1B Fig. 1C Fig. 1D

CABLE SLEEVE SYSTEM FOR BONE FIXATION

TECHNICAL FIELD

The present invention relates to a cable sleeve system for bone fixation, and in particular to a cable sleeve system comprising a sleeve consisting of a head and a piercing portion, and a cable. The cable sleeve system of the present invention is useful in the treatment of fractures in the femoral greater trochanter, olecranon, tibial tubercle and medial malleolus of the ankle, and in bone fixation following cutting operations involving such bone parts.

BACKGROUND OF THE INVENTION

Cases of osteoporosis are becoming increasingly common with the progress in the aging of the population, and this is in turn leading to an increasing number of cases requiring hip joint replacement such as hip joint fractures, coxarthrosis, and femoral head necrosis. Also, knee joint replacement is becoming increasingly common due to the increase in the cases of gonarthrosis. In particular, it is often necessary to cut off the greater trochanter in the case of a hip joint replacement operation, and to cut off the tibial tubercule in the case of a knee joint replacement, to gain access to the joint in either case. The separated bone part needs to be restored to the original state once the operation on the joint is completed. This is normally accomplished by the bone fixation method using screws, the bone fixation method bused on cable tensioning by using pins and a mild steel cable, or the bone fixation method using a cable grip and cable.

However, the methods based on the use of screws, pins and spikes are known to have problems because the fixation capability may be lost due to the loosening or breaking of the screws, pins and spikes, and the breaking of the mild steel cable. In case of the bone fixation method using a cable grip and cable, pain and inflammation in the tensor fascia lata muscle and bursa subcutanea trochanterica due to the presence of the cable grip may occur, and this is aggravated by the irritation of the soft body tissues by the cut ends of the cable. Should such an undesirable symptom develop, a reoperation would become necessary, and this would impose a serious burden on the patient. Also, because a bone fixation fixture is an foreign object which is embedded in the human body, it is desired to be as small as possible.

BRIEF SUMMARY OF THE INVENTION

The present invention was made with the aim to resolve such problems of the prior art, and its primary object is to provide a cable sleeve system for bone fixation, comprising a cable, and a sleeve including a head for securing the cable and a piercing portion, wherein the piercing portion projects from a bottom face of the head substantially perpendicularly therefrom, and the head is provided with a bore extending in parallel with the bottom face for securing the cable therein, the head being adapted to be crimped to secure the cable therein.

The sleeve according to the present invention comprises a head and a piercing portion, and may be additionally provided with a grip portion. The upper and lower faces of the head are defined by planes which are parallel to each other, and the head may have any desired shape, such as circular and polygonal shapes, but preferably has a rectangular shape in view of the ease of holding the head and securing the cable. In this case also, sharp corners should be appropriately chamfered so as to minimize irritations to the human body tissues. For the ease of handling the sleeve at the time of driving the piercing portion into the bone, normally, the top face of the head should be larger than the bottom face thereof. As a result, the longitudinal section of the head will have a trapezoidal shape.

The piercing portion is adapted to be driven into the bone and embedded therein, and has a tapered and pointed tip so as to be directly driven into the bone or drilled into the bone by using a drill which is operated either manually or by power. The piercing portion consists of a pin or spikes. In the case of a pin, it typically projects substantially centrally and perpendicularly from the bottom face of the head. The pin includes a part of a relatively constant thickness located adjacent to the head and an end part which is tapered and pointed. The spikes are typically paired on either end of the head, and are each generally tapered and provided with a pointed end.

The sleeve head is provided with a bore for securing the cable therein. The cable fixation bore may consist of a pair of circular bores or a single bore having a cross section in the shape of numeral 8, in each case, extending linearly across the head in parallel with the bottom face of the head. The cable fixation bore is used for securing the cable therein under a prescribed tension for the purpose of firmly closing the fracture plane or cut plane of the bone part at a prescribed pressure.

The sleeve according to the present invention may be provided with a sleeve grip portion which extends centrally from the top face of the sleeve in the opposite direction from the piercing portion. The sleeve grip portion allows the sleeve to be held by hand in a stable manner when driving the piercing portion of the sleeve into the bone part, and is highly useful in simplifying the accurate position of the sleeve on the bone part. The length of the grip portion should be selected for each specific application, and is preferably in the range of about 5 to 10 cm in the case of a greater trochanter fixation. Once the pin is fully pierced into the bone part, and the cable is firmly secured, the sleeve grip portion is not necessary any more. Therefore, it is preferable to provide a notch in the grip portion so that the grip portion may be readily broken by hand at a part immediately above the sleeve without requiring any cutting tool.

The sleeve of the present invention may be made of ceramic materials such as hydroxyapatite, alumina, carbon, calcium phosphate, bioglass, crystallized glass, zirconia, silicon nitride and titanium oxide, metallic materials such as stainless steel, cobalt-chromium alloy, titanium, titanium alloy and tantalum, and polymer materials such as polymethyl-methacrylate, polysulfone, high density polyethylene and polylactic resins. From the viewpoint of mechanical strength, biocompatibility, corrosion resistance and durability cobalt-chromium alloy, titanium, titanium alloy and stainless steel are preferred. Titanium and titanium alloy are particularly preferred from the viewpoint of biocompatibility, corrosion resistance, resiliency, weight and handling. Stainless steel is preferred from the viewpoint of mechanical strength and securing capability. The cable used in the present invention may consist of any material as long as it has required flexibility, tensile strength and biocompatibility, but is preferably made of cobalt-chromium alloy, titanium, titanium alloy or stainless steel, and is more preferably made of the same material as the sleeve from the viewpoint of corrosion in the living body.

BRIEF DESCRIPTION OF THE DRAWINGS

FIGS. 1A–1D illustrate a sleeve of a bone fixation cable sleeve system incorporated with a pin embodying the present invention which is suitable for fixing fractures on the olecranon, tibial tubercle, and greater trochanter, FIGS. 1A, 1B, 1C, and 1D being side, front, plan, and bottom views thereof, respectively;

DETAILED DESCRIPTION OF THE PREFERRED EMBODIMENTS

Figure 2A:
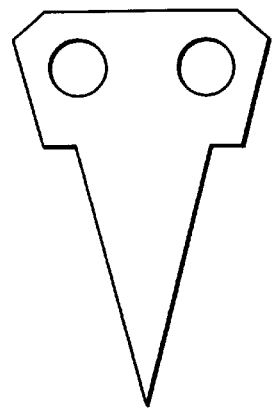
FIGS. 2A–2E illustrate a sleeve of a bone fixation cable sleeve system incorporated with spikes embodying the present invention which is particularly suitable for fixing fractures in the greater trochanter, FIGS. 2A, 2B, 2C, 2D, and 2E being side, front, plan, bottom, and perspective views thereof, respectively.
Figure 2B:
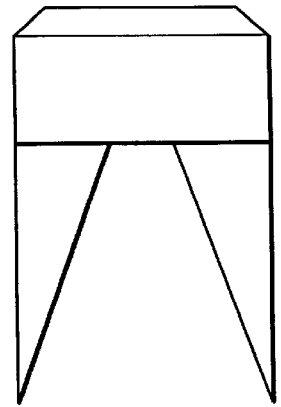
Figure 2C:
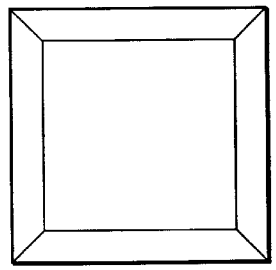
Figure 2D:
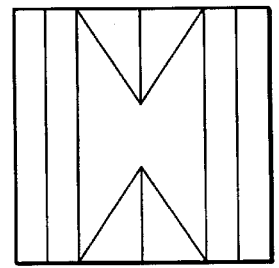
Figure 2E:
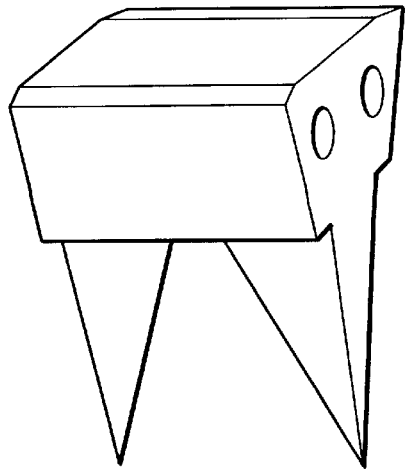

FIG. 1 illustrates a sleeve of a bone fixation cable sleeve system incorporated with a pin embodying the present invention. The sleeve system illustrated in FIG. 1 is particularly suitable for fixing fractures in the olecranon and medial malleolus of ankle, and, by changing the size, for fixing fractures in the greater trochanter. The embodiment shown in FIG. 1 is illustrated as being provided with ridges and corners which are not chamfered, but it is desirable to have such parts suitably chamfered so as not to irritate the body tissues.

A sleeve which is suitable for fixing fractures in the olecranon and medial malleolus of the ankle is provided with a grip portion 1 which is 1.8 to 2.5 mm in diameter. In the embodiment illustrated in FIGS. 1A–1D, the sleeve is provided with a head having an inverted trapezoidal shape as shown in FIG. 1B, although it may have any arbitrary shape. In this case, the cable being assumed to have a diameter in the range of 1.0 to 1.4 mm, the cable bore is provided with an inner diameter in the range of 1.0 to 1.4 mm so as to allow the cable to be passed therein. The thickness H of the sleeve head is 4 mm in this case, but is typically in the range of 2 to 5 mm. The width W and depth D of the head are both 8 mm, but are normally in the range of 5 to 15 mm, and may be either identical to or different from each other. The diameter of the pin is desirably in the range of 1.8 to 2.5 mm, and is 2.5 mm in the case of the embodiment illustrated in FIGS. 1A–1D. If the diameter is less than 1.8 mm, the fixation capability may not be adequate, and the pin could break. If the diameter is greater than 2.5 mm, the burden on the bone may become excessive.

A sleeve suitable for fixing the greater trochanter is required to have a somewhat larger size than a sleeve for fixing fractures of the olecranon or medial malleolus of the ankle because the former is subjected to a relatively large load as compared to the latter. The diameter of the grip portion 1 is likewise 2 to 3 mm, but the cable bore is in the range of 1.2 to 1.8 mm because of the need to pass through a thicker cable having a diameter in the range of 1.2 to 1.8 mm. The thickness H of the head of the sleeve is preferably in the range of 3 to 5 mm. The width W and depth D are each likewise in the range of 5 to 15 mm, and may be either identical to or different from each other. The pin serving as the bone piercing portion preferably has a diameter in the range of 2 to 3 mm. If the diameter is less than 2 mm, the pin may not have an adequate fixation capability to fix the greater trochanter, and could break. If the diameter is greater than 3 mm, the burden on the bone may become excessive.

When applying the sleeve to fixing the greater trochanter, the total length of the pin should be selected according to the state and configuration of the greater trochanter that is going to be treated. The total length of the pin should also be changed depending on whether a prosthetic joint is to be used in combination with the caput of bone or not. For instance, when a prosthetic joint is not to be used, such as when fixing a fracture of the greater trochanter, fixing the greater trochanter following a bone cutting operation such as when following a hip joint operation other than total hip replacement, or fixing a fracture of the tibial tubercle, the total length of the pin may be in the range of 40 to 100 mm so as to reach the cortical bone on the other side. When a prosthetic joint is to be used, the cable sleeve system should be incorporated with spikes having a length that would keep them from reaching the stem of the prosthetic joint.

FIGS. 2A–2E show a sleeve portion of a bone fixation cable sleeve system incorporated with spikes embodying the present invention which is particularly suitable for fixing the greater trochanter. In the case of the embodiment illustrated in FIGS. 2A–2E also, various parts should be chamfered so as to minimize irritations to body tissues. In this case, the thickness of the sleeve head is about 4 mm, and the width and depth of the head are about 8 mm and about 10 mm respectively. A spike is formed on each end of the sleeve, and these two spikes effectively prevent the sleeve from moving or turning when subjected to an external force. The length of each spike is in the range of 4 to 10 mm. If the length is less than 4 mm, the fixation capability may not be adequate. If the length is greater than 10 mm, the burden on the bone when piercing the bone may become excessive, and the bone could be damaged.

Figure 3:
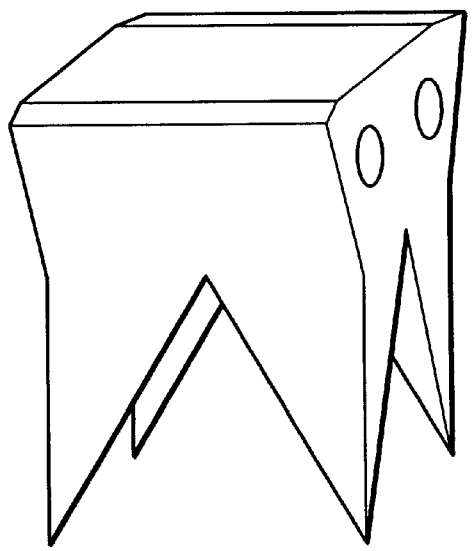
FIG. 3 illustrates a sleeve of a bone fixation cable sleeve system incorporated with spikes embodying the present invention which is provided with four legs.

FIG. 3 illustrates a bone fixation cable system incorporated with spikes having a spike on each corner of the bottom face thereof according to the present invention.

Figure 4A:
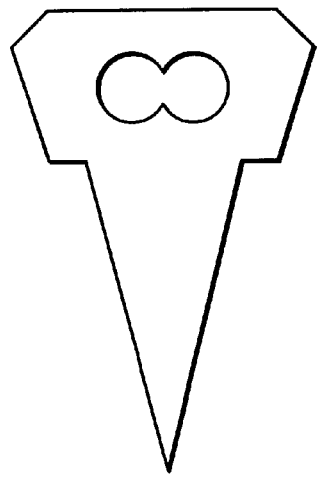
FIGS. 4A and 4B show front views of sleeves of two different embodiments each having a cable bore in the shape of a number 8 which is formed by merging two cable bores together, FIG. 4A being an embodiment provided with two spikes each having a stepped side, and FIG. 4B being an embodiment provided with four spikes.
Figure 4B:
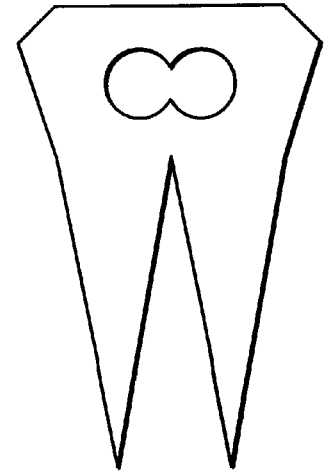

FIGS. 4A and 4B illustrate a sleeve incorporated with spikes which is provided with a cable bore having the shape of a number 8 created by merging two cable bores into one. By thus merging two cable bores into one, it becomes possible to fix the cable more firmly. It is also possible to have a sleeve incorporated with a pin to be similarly provided with a single cable bore having the shape of a number 8.

The procedure of fixing the cut greater trochanter in the case of not using a prosthetic joint by using a bone fixation cable sleeve system incorporated with a pin according to the present invention is described in the following. First of all, the cut greater trochanter is accurately reposited. A pin having a prescribed length is attached to a drill which may be either manually or power operated, and is driven into the greater trochanter until the tip of the rotating pin reaches the cortical bone on the other side. A cable is passed through a hole which is formed in advance in the femoral trochanter section by another drill bit, and then passed through the two cable bores of the sleeve from two different ends. The cable is lightly tensioned by hand, and is then suitably tensioned by using a special tensioner. With the cable thus tensioned, the sleeve is crimped onto the cable to secure the cable to the sleeve. The cable is then cut by using a cable cutter. The greater trochanter can be similarly fixed, and an adequate fixing result can be achieved by using a pair of cable sleeve systems incorporated with a pin or spikes.

In the case of a cable sleeve system incorporated with spikes, the cable can be fixed by striking the sleeve from above after placing the sleeve at a prescribed point. Because a cable sleeve system incorporated with spikes cannot be turned once it is fixed on the bone, it is important to heed the direction of the cable bores when striking the sleeve into the bone.

The cable used in the present invention may consist of a mono-filament cable, but more preferably consists of a multi-filament cable to achieve a desired resiliency. The thickness of the cable is preferably in the range of 1 to 3 mm, and more preferably in the range of 1.2 to 2.5 mm. If the cable thickness is less than 1 mm, the cable may break, or the bone may be damage when subjected to an external force. If the cable thickness is greater than 3 mm, the cable sleeve may be required to be excessively increased in size so as to match the cable thickness.

From the viewpoint of resiliency and mechanical strength, the multi-filament cable preferably consists of a double-multi-filament cable which is formed by twining several strands each formed by twining several filaments all in a same direction.

When the conventional cable grip is used, because a large grip end is secured to the greater trochanter, and protrudes out of the bone, inflammation and hemorrhage tend to develop due to irritations to the body tissues, and pain and inflammation in the tensor fascia lata muscle and bursa subcutanea trochanterica are not uncommon. According to the present invention, because the sleeve is highly compact, and the protrusion from the greater trochanter can be kept minimal, such undesirable side effects can be avoided.

FIGS. 1A–1D illustrate a sleeve of a bone fixation cable sleeve system incorporated with a pin embodying the present invention. FIGS. 2A–2E illustrate a sleeve of a bone fixation cable sleeve system incorporated with spikes embodying the present invention. FIG. 3 illustrates a sleeve of a bone fixation cable sleeve system incorporated with four spikes embodying the present invention. FIGS. 4A and 4B show simplified front views of sleeves having a cable bore in the shape of a number 8.

INDUSTRIAL APPLICABILITY

Because the sleeve can be made highly compact, it is possible to avoid undesirable side effects such as hemorrhage and inflammation due to irritations to the human body tissues which occurred frequently in the case of the cable securing method using the conventional cable grip.

What is claimed is:

1. A cable sleeve system for bone fixation, comprising a cable, and a sleeve including a head for securing the cable and a piercing portion, wherein the piercing portion projects from a bottom face of the head substantially perpendicularly therefrom, and the head is provided with a bore extending in parallel with the bottom face for securing the cable therein, the head being adapted to be crimped to secure the cable therein, wherein the sleeve is provided with a sleeve grip portion, and wherein the sleeve grip portion is provided with a notch in a part immediately above the head.

2. A cable sleeve system for bone fixation according to claim 1, wherein the piercing portion consists of a pin projecting centrally from the head.

3. A cable sleeve system for bone fixation according to claim 1, wherein the system is adapted for the fixation of a greater trochanter.

4. A cable sleeve system for bone fixation according to claim 3, wherein the piercing portion has a diameter in the range of 2.0 to 3.0 mm and a piercing length in the range of 40 to 100 mm, and the cable has a thickness in the range of 1.2 to 1.8 mm.

5. A cable sleeve system for bone fixation according to claim 1, wherein the system is adapted for the fixation of an olecranon or medial malleolus of an ankle.

6. A cable sleeve system for bone fixation according to claim 5, wherein the piercing portion has a diameter in the range of 1.8 to 2.5 mm and a piercing length in the range of 40 to 100 mm, and the cable has a thickness in the range of 1.0 to 1.4 mm.

7. A cable sleeve system for bone fixation according to claim 1, wherein the piercing portion consists of paired spikes being separated along a line which is parallel with the axis of the bore.

8. A cable sleeve system for bone fixation according to claim 7, wherein the spikes each have a length in the range of 4 to 10 mm.

9. A cable sleeve system for bone fixation according to claim 1, comprising a pair of cable bores each allowing the cable to be passed freely.

10. A cable sleeve system for bone fixation according to claim 1, wherein the sleeve and cable are made of titanium or titanium alloy.

11. A cable sleeve system for bone fixation according to claim 1, wherein the sleeve and cable are made of stainless steel.

12. A cable sleeve system for bone fixation according to claim 1, wherein the piercing portion comprises spikes projecting perpendicularly from a plane which is parallel with the plane of the bore.

13. A sleeve for bone fixation, comprising:

a head capable of securing a cable, the head being provided with a bore extending in parallel with a bottom face of the head for securing the cable therein, and the head being adapted to be crimped to secure the cable therein;

a piercing portion projecting from the bottom face of the head; and a sleeve grip portion provided with a notch in a part immediately above the head.

14. The sleeve of claim 13, wherein the piercing portion comprises a pin.

15. The sleeve of claim 13, wherein the piercing portion comprises a spike.

16. The sleeve of claim 13, wherein a portion of the sleeve comprises one or more of Titanium, Titanium alloy, or stainless steel.

* * * * *